United States Patent [19]
Anton et al.

[11] Patent Number: 5,180,846
[45] Date of Patent: Jan. 19, 1993

[54] HYDROGENATION OF ENZYMATICALLY-PRODUCED GLYCOLIC ACID/AMINOMETHYLPHOSPHONIC ACID MIXTURES

[75] Inventors: David L. Anton; Robert DiCosimo, both of Wilmington, Del.; Earnest W. Porta, Landenberg, Pa.

[73] Assignee: E. I. Du Pont de Nemours & Company, Wilmington, Del.

[21] Appl. No.: 788,648

[22] Filed: Nov. 6, 1991

[51] Int. Cl.$^5$ .............................................. C07F 9/38
[52] U.S. Cl. ..................................................... 562/17
[58] Field of Search ......................................... 562/17

[56] References Cited

U.S. PATENT DOCUMENTS

| | | | |
|---|---|---|---|
| 3,103,473 | 9/1963 | Juda | 204/77 |
| 3,281,460 | 10/1966 | Gandon | 260/530 |
| 3,361,653 | 1/1968 | Miller | 204/74 |
| 3,927,080 | 12/1975 | Gaertmer | 562/17 |
| 3,956,370 | 5/1976 | Parry | 562/17 |
| 3,959,361 | 5/1976 | Krueger et al. | 562/17 |
| 4,033,896 | 7/1977 | Mitchell | 562/617 |
| 4,047,927 | 9/1977 | Gaertner | 562/17 |
| 4,073,804 | 2/1978 | Hearon et al. | 260/534 |
| 4,094,928 | 6/1978 | Gaertner et al. | 260/944 |
| 4,146,731 | 3/1979 | Ogahara et al. | 562/531 |
| 4,233,056 | 11/1980 | Maier | 562/17 |
| 4,233,452 | 11/1980 | Williams et al. | 549/79 |
| 4,235,684 | 11/1980 | Harada et al. | 204/79 |
| 4,369,142 | 1/1983 | Moser | 562/17 |
| 4,405,531 | 9/1983 | Franz | 260/501.12 |
| 4,455,371 | 6/1984 | Richardson et al. | 435/25 |
| 4,650,613 | 3/1982 | Pulwer | 562/17 |
| 4,670,191 | 6/1987 | Kleiner | 562/17 |
| 4,851,159 | 7/1989 | Fields et al. | 562/17 |
| 4,871,669 | 10/1989 | Murray et al. | 435/147 |
| 4,921,991 | 5/1990 | Lacroix | 562/17 |
| 5,041,627 | 8/1991 | Baysdon | 560/16 |

FOREIGN PATENT DOCUMENTS

| | | |
|---|---|---|
| 1039739 | 7/1981 | Canada . |
| 0079767 | 5/1983 | European Pat. Off. . |
| 0186648 | 12/1985 | European Pat. Off. . |
| 02144578 | 3/1987 | European Pat. Off. . |
| 0413672 | 2/1991 | European Pat. Off. . |
| 0133387 | 11/1986 | Poland . |
| 2034313 | 6/1980 | United Kingdom . |

OTHER PUBLICATIONS

Gaylord "Reduction with Complex Metal Hydrides", Interscience Publishers, Inc. New York 1956 pp. ix-xvi and pp. 789-790, 806.
Wagner and Zook, "Synthetic Organic Chemistry" John Wiley & Sons, Inc. 1953, pp. 660-663-chapter 24.
Tolbert et al., "J. Biol. Chem." vol. 181 pp. 905-914 (1949).
Richardson et al., "J. Biol. Chem." vol. 236 pp. 1280-1284 (1961).
Clagette et al., "J. Biol. Chem.", vol. 178 pp. 977-987 (1961).
Zelitch et al., "J. Biol. Chem." vol. 201 pp. 707-718 (1953).
Robinson et al, "J. Biol. Chem.," vol. 237, pp. 2001-2009 (1962).
Frigerio et al., "J. Biol. Chem.," vol. 231 pp. 135-157 (1958).
Zelitch et al., "Methods in Enzymology" vol. 1 pp. 528-532 (1955).
Nishimura et al., "Arch. Biochem. Biophys." vol. 222 pp. 397-402 (1983).
Asker et al., "Biochim Biophys. Acta" vol. 761 pp. 103-108 (1983).
Emes et al, "Int. J. Biochem.", vol. 16 1373-1378 (1984).
Cederlund et al, "Eur. J. Biochem." vol. 173 pp. 523-530 (1988).
Lindquist et al., "J. Biol. Chem." vol. 264 pp. 3624-3628 (1989).
Yagai, "Methods of Biochemical Analysis," vol. X pp. 319-355 (1962).
Volokito et al., "J. Biol. Chem." vol. 262, 15825 (1987).
Ullmans Encyklopadie der technischen chemie 4th ed., vol. 12, Verlag Chemie, Weinheim 1976, 381.
Macheroux et al., "Biochemistry", vol. 30 ppl. 4612-4619 (1991).

Primary Examiner—Paul J. Killos
Attorney, Agent, or Firm—Robert B. Stevenson

[57] ABSTRACT

The invention provides a process for the production of N-(phosphonomethyl)glycine, also known as glyphosate. The process comprises hydrogenating a mixture containing glyoxylic acid and aminomethylphosphonic acid, the mixture having been enzymatically prepared in situ by the reaction of glycolic acid and oxygen in an aqueous solution containing aminomethylphosphonic acid and the enzymes glycolate oxidase and catalase.

9 Claims, No Drawings

HYDROGENATION OF ENZYMATICALLY-PRODUCED GLYCOLIC ACID/AMINOMETHYLPHOSPHONIC ACID MIXTURES

BACKGROUND OF THE INVENTION

1. Field of the Invention

This invention relates to the preparation of N-(posphonomethyl)glycine by the hydrogenation of mixtures produced by the reaction of glycolic acid and oxygen in an aqueous solution containing aminomethylphosphonic acid (AMPA) and the enzymes glycolate oxidase ((S)-2-hydroxy-acid oxidase, EC 1.1.3.15) and catalase (EC 1.11.1.6). N-(Phosphonomethyl)glycine is a broad-spectrum, post-emergent herbicide useful in controlling the growth of a wide variety of plants.

2. Description of the Related Art

Numerous methods are known for preparing N-(phosphonomethyl)glycine from aminomethylphosphonic acid and glyoxylic acid. One such method, described in Rogers et al., European Patent Application 186,648, involves condensation of glyoxylic acid or a salt thereof with aminomethylphosphonic acid or a salt thereof to form an intermediate product, generally regarded as an aldimine (Schiff base), which without isolation is reduced, as by catalytic hydrogenation, to N-(phosphonomethyl)glycine. A second method, described in Gaertner, U.S. Pat. No. 4,094,928, isolates these same intermediate carbonylaldiminomethanephosphonates by the reaction of glyoxylic acid esters with aminomethylphosphonate esters in a non-aqueous solvent; after azeotropic distillation of water and removal of the solvent, the carbonylaldiminomethanephosphonate ester is reduced and the ester groups hydrolyzed to produce N-(phosphonomethyl)glycine.

The above routes to N-(phosphonomethyl)glycine suffer in that glyoxylic acid is a rather costly starting material, and other less expensive routes to the desired material are practiced. Existing methods for the preparation of glyoxylic acid, such as hydrolysis of a dihaloacetic acid, electrolytic reduction of oxalic acid, oxidation of glyoxal, catalytic oxidation of ethylene or acetaldehyde, and ozonolysis of maleic acid, its esters or anhydride, present one or more difficulties in practice, e.g. costly separation/purification steps, low yields, or large waste streams. The method described in Gaertner is also disadvantageous in that it requires several additional steps (with corresponding losses in yield), and the unnecessary isolation of an intermediate.

Another method for the synthesis of N-(phosphonomethyl)glycine, disclosed in Kleiner, U.S. Pat. No. 4,670,191, comprises the reaction of aminomethylphosphonic acid or a salt thereof with about two molar equivalents of glyoxylic acid in aqueous medium. The excess glyoxylic acid evidently functions as a reducing agent, converting an intermediate glyoxylic acid-aminomethylphosphonic acid reaction product to the desired N-(phosphonomethyl)glycine, and is itself oxidized to one or more by-products, including $CO_2$. Similarly, Fields et al., in U.S. Pat. No. 4,851,159 prepare N-(phosphonomethyl)glycine by heating an N-acylaminomethylphosphonic acid with glyoxylic acid or a derivative thereof. The mole ratio of the glyoxylic to the N-acylamino component is preferably 2 to 1; otherwise at smaller ratios the yield suffers.

The Kleiner and Fields et al. processes entail the disadvantages of not only employing relatively expensive glyoxylic acid but of employing it as a sacrificial reductant (ca. one mole of glyoxylate employed as reductant for every mole of N-(phosphonomethyl)glycine produced) as well as the condensing agent for the amino-(or N-acylamino) methylphosphonic acid.

SUMMARY OF THE INVENTION

The process for preparing N-(phosphonomethyl)glycine according to the present invention involves hydrogenating a mixture, wherein the mixture is enzymatically produced by reacting glycolic acid and oxygen in an aqueous solution containing aminomethylphosphonic acid (AMPA) and the enzymes glycolate oxidase and catalase. It should be appreciated for purposes of this invention that mixtures, so produced, inherently result in a distribution of oxidation by-products in addition to the desired glyoxylic acid component (including by way of example but not limited thereto, oxalate, formate, and carbon dioxide). Also present in such mixtures will be unreacted glycolate as well as various additives such as flavin mononucleotide (hereinafter referred to as FMN) or the like, all of which may or may not influence the desired hydrogenation reaction (again by way of example, but not limited thereto, it has been found that both formate and FMN lower the recovered carbon balance when present during the hydrogenation of glyoxylic acid in the presence AMPA).

Thus the present invention provides an improved process for preparing N-(phosphonomethyl)glycine comprising the step of reducing a mixture of glyoxylic acid and aminomethylphosphonic acid by hydrogenation; said mixture being enzymatically generated in situ in an aqueous solution by incorporating into the aqueous solution glycolic acid, a first catalyst adapted to catalyze the oxidation of glycolic acid with oxygen to glyoxylic acid and hydrogen peroxide, and a second catalyst adapted to catalyze the decomposition of hydrogen peroxide, adjusting the pH of the solution to between 7 and about 10, contacting the solution with a source of oxygen at an effective temperature and sufficient time to convert at least a portion of the glycolic component to the glyoxylic component in the presence of aminomethylphosphonic acid, and ceasing contacting the solution with oxygen prior to the reducing step.

Preferably, the catalysts are enzymatic; more preferably the first enzyme is glycolate oxidase ((S)-2-hydroxy-acid oxidase, EC 1.1.3.15) and the second enzyme is catalase (EC 1.11.1.6). After the contacting of the solution with $O_2$ in the presence of the catalysts/enzymes is ceased, the catalysts/enzymes are removed, as by filtration or centrifugation, before the solution is subjected to reducing conditions for the production of N-(phosphonomethyl)glycine.

Thus, by obviating the need to prepare glyoxylic acid in a separate step, the present invention provides for a more efficient and economic process for the production of N-(phosphonomethyl)glycine.

It is an object of this invention to provide an improved process for the production of N-(phosphonomethyl)glycine by reduction of mixtures of glyoxylic acid and aminomethylphosphonic acid which avoids the need to separately prepare glyoxylic acid.

Another object is to provide such a process wherein glyoxylic acid is enzymatically generated in situ in the presence of aminomethylphosphonic acid from a readily available precursor thereof, namely glycolic acid, thereby affording a more efficient and economic process for the production of N-(phosphonomethyl)glycine.

DESCRIPTION OF THE PREFERRED EMBODIMENTS

The improved process for the production of N-(phosphonomethyl)glycine according to the present invention involves the reduction of a mixture containing glyoxylic acid (or a suitable derivative thereof) with aminomethylphosphonic acid (AMPA) (or a suitable derivative thereof). Prefferably, the mixture is prepared by catalytically oxidizing a glycolic acid component or a suitable salt thereof by contacting the glycolic acid component with a source of molecular oxygen in the presence of AMPA and a catalyst effective to catalyze the reaction of glycolic acid with $O_2$ to form glyoxylic acid. One such catalyst is a naturally-occurring enzyme glycolate oxidase (EC 1.1.3.15), also known as glycolic acid oxidase, which is capable of catalyzing acid the reaction to produce glyoxylic acid in high yields at high glycolic acid conversions in aqueous media under mild conditions of pH and temperature, i.e.,

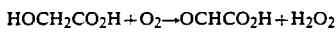

$$HOCH_2CO_2H + O_2 \rightarrow OCHCO_2H + H_2O_2$$

Optimal results in the use of glycolate oxidase as a catalyst for the oxidative conversion of glycolic acid to glyoxylic acid are obtained by incorporating into the reaction solution a catalyst for the decomposition of hydrogen peroxide. One such peroxide-destroying catalyst which is effective in combination with glycolate oxidase is the enzyme catalase (E.C. 1.11.1.6). Catalase catalyzes the decomposition of hydrogen peroxide to water and oxygen, and it is believed to improve yields of glyoxylic acid by accelerating the decomposition of the hydrogen peroxide produced as a byproduct with glyoxylic acid in the glycolate oxidase-catalyzed reaction of glycolic acid with $O_2$. The concentration of catalase should be 50 to 50,000 IU/mL, preferably 500 to 15,000 IU/mL. It is preferred that the catalase and glycolate oxidase concentrations be adjusted within the above ranges so that the ratio (measured in IU for each enzyme) of catalase to glycolate oxidase is at least about 250:1.

Another optional but often beneficial ingredient in the reaction solution is flavin mononucleotide (FMN), which is generally used at a concentration of 0.0 to about 2.0 mM, preferably about 0.01 to about 0.2 mM. It is believed the FMN increases the productivity of the glycolate oxidase, by which is meant the amount of glycolic acid converted to glyoxylic acid per unit of enzyme. It is to be understood that the concentration of added FMN is in addition to any FMN present with the enzyme, because FMN is often also added to the enzyme during the preparation of the enzyme. The structure of FMN and a method for its analysis is found in K. Yagai, *Methods of Biochemical Analysis*, Vol. X, Interscience Publishers, New York, 1962, p. 319–355, which is hereby included by reference.

Glycolic acid (2-hydroxyacetic acid) is employed in the present reaction at an initial concentration in the range of 0.10M to 2.0M, preferably between 0.25M and 1.0M. It can be used as such or as a compatible salt thereof, that is, a salt that is water-soluble and whose cation does not interfere with the desired conversion of glycolic acid to glyoxylic acid, or the subsequent reaction of the glyoxylic acid product with the aminomethylphosphonic acid to form N-(phosphonomethyl)glycine. Suitable and compatible salt-forming cationic groups are readily determined by trial. Representative of such salts are the alkali metal, alkaline earth metal, ammonium, substituted ammonium, phosphonium, and substituted phosphonium salts.

The conversion of glycolic acid to glyoxylic acid is conveniently and preferably conducted in aqueous media. Aminomethylphosphonic acid (AMPA), or a suitable salt thereof, is added to produce a molar ratio of AMPA/glycolic acid (starting amount) in the range of from 0.01/1.0 to 3.0/1.0, preferably from 0.25/1.0 to 1.05/1.0. After combining AMPA and glycolic acid in an aqueous solution, the pH of the resulting mixture is adjusted to a value between 6 and 10, preferably between 7.0 and 8.5. Within this pH range, the exact value may be adjusted to obtain the desired pH by adding any compatible, non-interfering base, including alkali metal hydroxides, carbonates, bicarbonates and phosphates. The pH of the reaction mixture decreases slightly as the reaction proceeds, so it is often useful to start the reaction near the high end of the maximum enzyme activity pH range, about 9.0–8.5, and allow it to drop during the reaction. The pH can optionally be maintained by the separate addition of a non-interfering inorganic or organic buffer, since enzyme activity varies with pH.

It is understood that glycolic and glyoxylic acids are highly dissociated in water, and at pH of between 7 and 10 are largely if not substantially entirely present as glycolate and glyoxylate ions. It will be also be appreciated by those skilled in the art that glyoxylic acid (and its conjugate base, the glyoxylate anion) may also be present as the hydrate, e.g. $(HO)_2CHCOOH$ and/or as the hemiacetal, $HOOCCH(OH)OCH(OH)COOH$, which compositions and their anionic counterparts are equivalent to glyoxylic acid and its anion for the present purpose of being suitable reactants for N-(phosphonomethyl)glycine formation.

Oxygen ($O_2$), the oxidant for the conversion of the glycolic acid to glyoxylic acid, may be added as a gas to the reaction by agitation of the liquid at the gas-liquid interface or through a membrane permeable to oxygen. It is believed that under most conditions, the reaction rate is at least partially controlled by the rate at which oxygen can be dissolved into the aqueous medium. Thus, although oxygen can be added to the reaction as air, it is preferred to use a relatively pure form of oxygen, and even use elevated pressures. Although no upper limit of oxygen pressure is known, oxygen pressures up to 50 atmospheres may be used, and an upper limit of 15 atmospheres is preferred. Agitation is important to maintaining a high oxygen dissolution (hence reaction) rate. Any convenient form of agitation is useful, such as stirring. On the other hand, as is well known to those skilled in the enzyme art, high shear agitation or agitation that produces foam may decrease the activity of the enzyme(s), and should be avoided.

The reaction temperature is an important variable, in that it affects reaction rate and the stability of the enzymes. A reaction temperature of 0° C. to 40° C. may be used, but the preferred reaction temperature range is from 5° C. to 15° C. Operating in the preferred temperature range maximizes recovered enzyme activity at the end of the reaction. The temperature should not be so low that the aqueous solution starts to freeze. Temperature can be controlled by ordinary methods, such as, but not limited to, by using a jacketed reaction vessel and passing liquid of the appropriate temperature through the jacket. The reaction vessel may be constructed of any material that is inert to the reaction ingredients.

Upon completion of the reaction, the enzymes may be removed by filtration or centrifugation and reused. Alternatively, they can be denatured by heating, e.g., to 70° C. for 5 minutes, and/or they can be allowed to remain in the reaction mixture if their presence in the subsequent steps of converting the glyoxylic-aminomethylphosphonic acid mixture to N-(phosphonomethyl)glycine and of recovering N-(phosphonomethyl)glycine from the reaction mixture is not objectionable. Flavin mononucleotide (FMN) may optionally be removed by contacting the solution with decolorizing carbon.

Following the cessation of contacting the reaction solution with $O_2$ and preferably following the removal of the enzyme glycolate oxidase and the enzyme catalase when present, the solution containing glyoxylic acid and aminomethylphosphonic acid (which are believed to be in equilibrium with the corresponding imine), is treated in accordance with any of the processes known to the art for producing N-(phosphonomethyl)glycine.

Catalytic hydrogenation is a preferred method for preparing N-(phosphonomethyl)glycine from a mixture of glyoxylic acid and aminomethylphosphonic acid. Catalysts suitable for this purpose include (but are not limited to) the various platinum metals, such as iridium, osmium, rhodium, ruthenium, platinum, and palladium; also various other transition metals such as cobalt, copper, nickel and zinc. The catalyst may be unsupported, for example as Raney nickel or platinum oxide; or it may be supported, for example as platinum on carbon, palladium on alumina, or nickel on kieselguhr. Palladium on carbon, nickel on kieselguhr and Raney nickel are preferred.

The hydrogenation can be performed at a pH of from 4 to 11, preferably from 5 to 10. Within this pH range, the exact value may be adjusted to obtain the desired pH by adding any compatible, non-interfering base or acid. Suitable bases include, but are not limited to, alkali metal hydroxides, carbonates, bicarbonates and phosphates, while suitable acids include, but are not limited to, hydrochloric, sulfuric, or phosphoric acid.

The hydrogenation temperature and pressure can vary widely. The temperature may generally be in the range of 0° C. to 150° C., preferably from 20° C. to 90° C., while the $H_2$ pressure is generally in the range of from about atmospheric to about 100 atmospheres, preferably from 1 to 10 atmospheres. The hydrogenation catalyst is employed at a minimum concentration sufficient to obtain the desired reaction rate and total conversion of starting materials under the chosen reaction conditions; this concentration is easily determined by trial. The catalyst may be used in amounts of from 0.001 to 20 or more parts by weight of catalyst per 100 parts of combined weight of the glyoxylic acid and AMPA employed in the reaction.

N-(Phosphonomethyl)glycine, useful as a post-emergent herbicide, may be recovered from the reduced solution, whatever the reducing method employed, by any of the recovery methods known to the art, including those disclosed in the U.S. Pat. Nos. 4,851,159 and 4,670,191 and in European Patent Applications 186 648 and 413 672.

In the following Examples, which serve to further illustrate the invention, the yields of glyoxylate, formate and oxalate, and the recovered yield of glycolate, are percentages based on the total amount of glycolic acid present at the beginning of the reaction. Analyses of reaction mixtures were performed using high pressure liquid chromatography. Organic acid analyses were performed using a Bio-Rad HPX-87H column, and AMPA and N-(phosphonomethyl)glycine were analyzed using a Bio-Rad Aminex glyphosate analysis column. Reported yields of N-(phosphonomethyl)glycine are based on either glyoxylate or AMPA, depending on which was the limiting reagent in the reaction.

EXAMPLE 1

Into a 3 oz. Fischer-Porter glass aerosol reaction vessel was placed a magnetic stirring bar and 10 mL of an aqueous solution containing glycolic acid (0.50M), aminomethylphosphonic acid (AMPA, 0.40 m), FMN (0.01 mM), butyric acid (HPLC internal standard, 0.10M), glycolate oxidase (from spinach, 1.0 IU/mL), and catalase (from *Aspergillus niger*, 14,000 IU/mL) at pH 8.5. The reaction vessel was sealed and the reaction mixture was cooled to 5° C., then the vessel was flushed with oxygen by pressurizing to 70 psig and venting to atmospheric pressure five times with stirring. The vessel was then pressurized to 70 psig of oxygen and the mixture stirred at 5° C. Aliquots (0.10 mL) were removed by syringe through a sampling port (without loss of pressure in the vessel) at regular intervals for analysis by HPLC to monitor the progress of the reaction. After 17.5 h, the HPLC yields of glyoxylate, formate, and oxalate were 91.0%, 2.9%, and 2.9%, respectively, and 4.1% glycolate remained. The final pH of the reaction mixture was 6.7.

The resulting mixture of glyoxylic acid (0.46M) and AMPA (0.40M) was filtered using an Amicon Centriprep 10 concentrator (10,000 molecular weight cutoff) to remove the soluble enzymes, then the filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi with hydrogen and stirred at 25° C. After 17 h, the concentration of N-(phosphonomethyl)glycine (determined by HPLC) was 0.29M (72% yield based on AMPA).

EXAMPLE 2

The enzymatic oxidation of glycolic acid in Example 1 was repeated, using 10 mL of an aqueous solution containing glycolic acid (0.25M), aminomethylphosphonic acid (AMPA, 0.20M), FMN (0.01 mM), butyric acid (HPLC internal standard, 0.10M), glycolate oxidase (from spinach, 1.0 IU/mL), and catalase (from *Aspergillus niger*, 14,000 IU/mL) at pH 8.5. After 6 h, the HPLC yields of glyoxylate, formate, and oxalate were 92.3%, 4.36%, and 5.5%, respectively, and no glycolate remained. The final pH of the reaction mixture was 6.7.

The resulting mixture of glyoxylic acid (0.23M) and AMPA (0.20M) was filtered using an Amicon Centriprep 10 concentrator (10,000 molecular weight cutoff) to remove the soluble enzymes, then the filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi with hydrogen and stirred at 25° C. After 17 h, the concentration of N-(phosphonomethyl)glycine (determined by HPLC) was 0.13M (66% yield based on AMPA).

EXAMPLE 3

The enzymatic oxidation of glycolic acid in Example 1 was repeated, using 10 mL of an aqueous solution containing glycolic acid (0.75 M), aminomethylphosphonic acid (AMPA, 0.60M), FMN (0.01 mM), butyric acid (HPLC internal standard, 0.10M), glycolate oxidase (from spinach, 2.0 IU/mL), and catalase (from *Aspergillus niger*, 14,000 IU/mL) at pH 8.5. After 40 h, the HPLC yields of glyoxylate, formate, and oxalate were 83.2%, 2.3%, and 7.5%, respectively, and no glycolate remained. The final pH of the reaction mixture was 6.8.

The resulting mixture of glyoxylic acid (0.62M) and AMPA (0.60M) was filtered using an Amicon Centriprep 10 concentrator (10,000 molecular weight cutoff) to remove the soluble enzymes, then the filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi with hydrogen and stirred at 25° C. After 24 h, the concentration of N-(phosphonomethyl)glycine (determined by HPLC) was 0.42M (70% yield based on AMPA).

EXAMPLE 4

The enzymatic oxidation of glycolic acid in Example 1 was repeated, using 10 mL of an aqueous solution containing glycolic acid (1.0M), aminomethylphosphonic acid (AMPA, 0.80M), FMN (0.01 mM), butyric acid (HPLC internal standard, 0.10M), glycolate oxidase (from spinach, 2.0 IU/mL), and catalase (from *Aspergillus niger*, 14,000 IU/mL) at pH 8.5. After 66 h, the HPLC yields of glyoxylate, formate, and oxalate were 78.9%, 2.2%, and 12.1%, respectively, and 2.0% glycolate remained. The final pH of the reaction mixture was 6.9.

The resulting mixture of glyoxylic acid (0.79M) and AMPA (0.80M) was filtered using an Amicon Centriprep 10 concentrator (10,000 molecular weight cutoff) to remove the soluble enzymes, then the filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi with hydrogen and stirred at 25° C. After 23 h, the concentration of N-(phosphonomethyl)glycine (determined by HPLC) was 0.51M (65% yield based on glyoxylic acid).

EXAMPLE 5

The enzymatic oxidation of glycolic acid in Example 1 was repeated, using 10 mL of an aqueous solution containing glycolic acid (025M), aminomethylphosphonic acid (AMPA, 0.263M), FMN (0.01 mM), butyric acid (HPLC internal standard, 0.25M), glycolate oxidase (from spinach, 1.0 IU/mL), and catalase (from *Aspergillus niger*, 14,000 IU/mL) at pH 7.0 and 15° C. After 8 h, the HPLC yields of glyoxylate, formate, and oxalate were 82.8%, 0.9%, and 2.1%, respectively, and 13.9% glycolate remained. The final pH of the reaction mixture was 6.6.

This mixture of glyoxylic acid (0.21M) and AMPA (0.263M) was filtered using an Amicon Centriprep 10 concentrator (10,000 molecular weight cutoff) to remove the soluble enzymes, then the filtrate and 50 mg of 10% Pd/C were placed in a stainless steel pressure vessel equipped with glass liner. The vessel was sealed, flushed with nitrogen gas, then pressurized to 1000 psi with hydrogen gas and shaken at 25° C. The pressure in the vessel fell to a stable value in the first 0.5 h of reaction, and the vessel was then repressurized to 1000 psi. After 4 h, the pressure in the vessel was vented, and the vessel flushed with nitrogen. The concentration of N-(phosphonomethyl)glycine (determined by HPLC) was 0.16M (76% yield based on glyoxylic acid).

EXAMPLE 6

The enzymatic oxidation of glycolic acid in Example 5 was repeated at pH 8. After 8 h, the HPLC yields of glyoxylate, formate, and oxalate were 86.7%, 1.8%, and 4.1%, respectively, and 13.2% glycolate remained. The final pH of the reaction mixture was 6.7.

This mixture of glyoxylic acid (0.22M) and AMPA (0.263M) was hydrogenated at 1000 psi using the same procedure as described in Example 5. After 4 h, the concentration of N-(phosphonomethyl)glycine (determined by HPLC) was 0.14M (64% yield based on glyoxylic acid).

EXAMPLE 7

The enzymatic oxidation of glycolic acid in Example 5 was repeated at pH 9. After 7 h, the HPLC yields of glyoxylate, formate, and oxalate were 70.0%, 5.6%, and 11.1%, respectively, and no glycolate remained. The final pH of the reaction mixture was 6.8.

This mixture of glyoxylic acid (0.18M) and AMPA (0.263M) was hydrogenated at 1000 psi using the same procedure as described in Example 5. After 4 h, the concentration of N-(phosphonomethyl)glycine (determined by HPLC) was 0.094M (52% yield based on AMPA).

EXAMPLE 8

The enzymatic oxidation of glycolic acid in Example 5 was repeated at pH 8.5, and using initial concentrations of glycolic acid and AMPA of 0.50M and 0.40M, respectively. After 16.5 h, the HPLC yields of glyoxylate, formate, and oxalate were 85.4%, 3.5%, and 6.3%, respectively, and 1.4% glycolate remained. The final pH of the reaction mixture was 7.0.

This mixture of glyoxylic acid (0.43M) and AMPA (0.40M) was hydrogenated at 1000 psi using the same procedure as described in Example 5. After 4 h, the concentration of N-(phosphonomethyl)glycine (determined by HPLC) was 0.30M (75% yield based on AMPA).

EXAMPLE 9

The enzymatic oxidation of glycolic acid in Example 1 was repeated, using 10 mL of an aqueous solution containing glycolic acid (0.50M), aminomethylphosphonic acid (AMPA, 0.375M), FMN (0.01 mM), butyric acid (HPLC internal standard, 0.10M), glycolate oxidase (from spinach, 1.0 IU/mL), and catalase (from *Aspergillus niger*, 14,000 IU/mL) at pH 8.5. After 17 h, the HPLC yields of glyoxylate, formate, and oxalate were 87.1%, 1.9%, and 2.1%, respectively, and 8.9% glycolate remained. The final pH of the reaction mixture was 6.7.

The resulting mixture of glyoxylic acid (0.435M) and AMPA (0.375M) was filtered using an Amicon Centriprep 10 concentrator (10,000 molecular weight cutoff) to remove the soluble enzymes, then the filtrate was mixed with 50 mg of decolorizing carbon (to remove FMN) and again filtered. The resulting filtrate was placed in a 3-oz. Fischer-Porter bottle equipped with a magnetic stirrer bar. To the bottle was then added 0.100 g of 10% Pd/C and the bottle sealed, flushed with nitrogen gas, then pressurized to 50 psi with hydrogen and stirred at 25° C. After 17 h, the concentration of N-(phosphonomethy)glycine (determined by HPLC) was 0.372M (99% yield based on AMPA).

We claim:

1. A process for preparing N-(phosphonomethyl)glycine which comprises hydrogenating a mixture, wherein said mixture is enzymatically produced by reacting glycolic acid and oxygen in an aqueous solution containing aminomethylphosphonic acid and the enzymes glycolate oxidase and catalase.

2. An improved process for preparing N-(phosphonomethyl)glycine comprising the step of reducing a mixture of glyoxylic acid and aminomethylphosphonic acid by hydrogenation; said mixture being enzymatically generated in situ in an aqueous solution by incorporating into the aqueous solution glycolic acid, aminomethylphosphonic acid, a first catalyst adapted to catalyze the oxidation of glycolic acid with oxygen to glyoxylic acid and hydrogen peroxide, and a second catalyst adapted to catalyze the decomposition of hydrogen peroxide, adjusting the pH of the solution to between 7 and about 10, contacting the solution with a source of oxygen at an effective temperature and sufficient time to convert at least a portion of the glycolic acid component to the glyoxylic acid component in the presence of aminomethylphosphonic acid, and ceasing contacting the solution with oxygen prior to the reducing step.

3. The process of claim 2 wherein the first catalyst is glycolate oxidase and the second catalyst is catalase.

4. The process of claim 1 wherein the hydrogenating is performed in the presence of a hydrogenation catalyst.

5. The process of claim 2 wherein the reducing is performed in the presence of a hydrogenation catalyst.

6. The process of claim 4 or 5 wherein the hydrogenation catalyst is selected from the group consisting of palladium on carbon, nickel on kieselguhr and Raney nickel.

7. The process of claim 6 wherein the hydrogenation catalyst is present in an amount of from 0.001 to 20 parts by weight catalyst per 100 parts of combined weight of the glyoxylic acid and aminomethylphosphonic acid employed.

8. The process of claim 7 wherein the hydrogenation is performed at a pH of from 4 to 11 within a temperature range of 0° C. to 150° C. and at a hydrogen pressure of 1 to about 100 atmospheres.

9. The process of claim 7 wherein the hydrogenation is performed at a pH of from 5 to 10 within a temperature range of 20° C. to 90° C. and at a hydrogen pressure of 1 to about 10 atmospheres.

* * * * *